United States Patent [19]

Barnett

[11] Patent Number: 4,717,546

[45] Date of Patent: Jan. 5, 1988

[54] GLUCOSE LEVEL MEASURING APPARATUS

[75] Inventor: J. Craig Barnett, Denver, Colo.

[73] Assignee: Texas Tech University Health Sciences Center, Lubbock, Tex.

[21] Appl. No.: 673,153

[22] Filed: Nov. 19, 1984

[51] Int. Cl.$^4$ .................. G01N 21/13; G01N 33/48; G01N 35/00

[52] U.S. Cl. .................................... 422/63; 422/68; 436/44

[58] Field of Search ............... 422/58, 63–66, 422/68; 436/66, 95, 169

[56] References Cited

U.S. PATENT DOCUMENTS

| | | | |
|---|---|---|---|
| 3,368,872 | 2/1968 | Natelson | 23/253 |
| 3,565,582 | 2/1971 | Young | 23/230 |
| 3,918,910 | 11/1975 | Soya et al. | 422/66 |
| 3,932,133 | 1/1976 | Ishikawa | 422/66 |
| 3,999,505 | 12/1976 | Kato et al. | 118/7 |
| 4,004,550 | 1/1977 | White et al. | 118/314 |
| 4,220,621 | 9/1980 | Simpson et al. | 422/100 |
| 4,296,069 | 10/1981 | Smith et al. | 422/64 |
| 4,311,667 | 1/1982 | Gocho | 422/100 |
| 4,420,564 | 12/1983 | Tsuji et al. | 435/288 |
| 4,425,427 | 1/1984 | Luderer | 435/10 |

Primary Examiner—Michael S. Marcus
Assistant Examiner—C. M. Delahunty
Attorney, Agent, or Firm—Walter C. Farley

[57] ABSTRACT

An apparatus for automatically performing a blood glucose test includes a cylindrical carrier with a holder for receiving a reagent pad. Upon receiving the pad, the carrier holds the pad for a predetermined reaction time and then rotates the pad successively to washing and de-watering stations. After de-watering, the pad is presented to a measuring station at which a reflectometer evaluates the color characteristics of the pad. A display of glucose level as a function of the color change of the pad is presented.

11 Claims, 19 Drawing Figures

GLUCOSE LEVEL MEASURING APPARATUS

This invention relates to an apparatus for performing tests to measure the amount of glucose in the blood with improved accuracy, repeatability and reliability.

BACKGROUND OF THE INVENTION

It is well known that measurements of blood glucose can be made by placing a drop of blood on a prepared reagent pad, allowing the blood to react with the materials on the pad for a fixed period of time, washing and then removing excess water from the pad, and then evaluating the color of the reacted area by comparison with a standard. The enzyme glucose oxidase catalyzes the oxidation of glucose in blood by oxygen in the atmosphere, producing gluconic acid and hydrogen peroxide. In the presence of peroxidase, chromogens in the reduced form are oxidized by the hydrogen peroxide and produce colors which range from gray to blue-purple. To avoid the inherent problems associated with visual comparison with a chart, a reflectometer using a light source, a photocell and electronic color evaluation is usable. One device suitable for this purpose is the blood glucose meter marketed by the Ames Division, Miles Laboratories, Inc., Elkhart, Ind.

While the theory is sound and while tests of this type can be performed to give accurate results, there are some serious practical problems in that the various steps must be performed with considerable precision in order for the results to be reliable. Specifically, the reaction time, i.e., the duration of the interval during which the blood is allowed to react with the materials in the pad, is quite critical.

Also, in order for the test results to be comparable, the washing must be performed in the same way each time and, after washing, the removal of excess water, often accomplished by blotting, must be done in a consistent fashion. If these steps are not done the same way each time, the blood samples from a single patient can be evaluated to indicate either a significant change in glucose level when none has actually occurred, or the reverse. While the experienced, skilled laboratory technician can obtain good results consistently, an inexperienced one may not. Of even more importance, a person attempting to perform the test at home may obtain widely varying measurements, resulting in over- or under-medication. It is important for some patients, particularly diabetics, to be able to conduct such tests on their own and the glucose meter mentioned above is sold for that purpose. However, unless the instructions are followed with precise consistency, it has been found that 30% or more of the measurements can be in error.

SUMMARY OF THE INVENTION

An objective of the present invention is to provide an apparatus which can perform blood glucose testing in a uniformly repeatable fashion with accurately and consistently performed and timed steps.

A further objective is to provide a testing device which is simple to use and which can be used by minimally trained individuals such as a patient doing a self-test.

Another objective is to provide a device which is not overly complicated and which can thus be produced at a reasonable price so as to be readily obtainable by individuals and small laboratories.

Briefly described, the invention comprises an apparatus for performing a test to determine the glucose level in a sample of blood placed on a reagent pad comprising the combination of means defining a receiving station, a wash station, a watering station and a measuring station in spaced relationship from each other and carrier means for holding the reagent pad, the carrier means being movable to transport the pad to each of the stations in sequence. Drive means is provided for moving the carrier means to transport the pad the stations and to hold the pad at those stations for preselected intervals of time. The wash station includes means for washing the pad when the carrier is moved to the wash station. The de-watering station includes means for removing superficial water which remains after the washing from the pad and the measuring station includes means for producing a signal representative of the color characteristics of the pad when the pad is presented to the measuring station. Finally, the apparatus includes means for receiving the signal and for producing a display representative of the glucose level in the blood sample.

BRIEF DESCRIPTION OF THE DRAWINGS

In order that the manner in which the advantages of the invention are attained can be understood in detail, a particularly advantageous embodiment thereof will be described with reference to the accompanying drawings, which form a part of this specification, and wherein.

DESCRIPTION OF THE PREFERRED EMBODIMENT

Referring first to FIGS. 1-4, a general description of the apparatus will be provided. The embodiment to be described is in the form of a portable apparatus usable to perform the necessary test under a variety of circumstances. As such, it is relatively small and is contained in a generally rectangular housing, various portions of which are omitted from the drawings so that the interior components can be more easily seen.

Within the testing apparatus, indicated generally at 20, is a generally cylindrical body 22 which is rotatable about its central axis in a manner to be described and which functions as a carrier for the reagent pad by which the test is performed. As seen in FIG. 2, carrier 22 is an elongated body one end of which protrudes through an opening 23 in and wall 24 of the housing. In the position shown in FIGS. 1-4, the rotatable carrier supports an axially extending strip holder 26 which can be caused to move axially with respect to carrier 22 for the purposes of receiving a test strip 27, withdrawing that strip into the apparatus during the test performance and then extending the strip for subsequent removal. The test strip 27 carrier a reagent pad 28 to which the drop of blood is applied for performing the test.

Although other test strips can be employed, the present apparatus is designed to use an existing test strip which is sold under the trademark DEXTROSTIX by Ames Division, Miles Laboratories, Inc., Elkhart, Ind. The DEXTROSTIX strips are relatively thin, flexible plastic strips having a width of about 3/16 inches and a length of about 3.25 inches. At one end of each such strip is a reagent pad having a width equal to that of the strip and a length of approximately 13/32 inches. The reagent pad is impregnated with the necessary reagent ingredients to accomplish the oxidation described above and the activity of the chromogens which produce a calibrated color change which is a function of glucose level in the sample supplied to the reagent pad. These specific pads are provided with 1.0 IU glucose oxidase; 1.14 IU peroxidase; 30 $\mu$g 3,3'-dimethyl, - 4,4'-diaminobiphenyl dihydrochloride; 20 $\mu$g 2,7'-diaminofluorene dihydrochloride; 50 $\mu$g 4,4'-diaminobiphenyldihydrochloride; and 96% w/v nonreactive ingredients.

Figure 1:
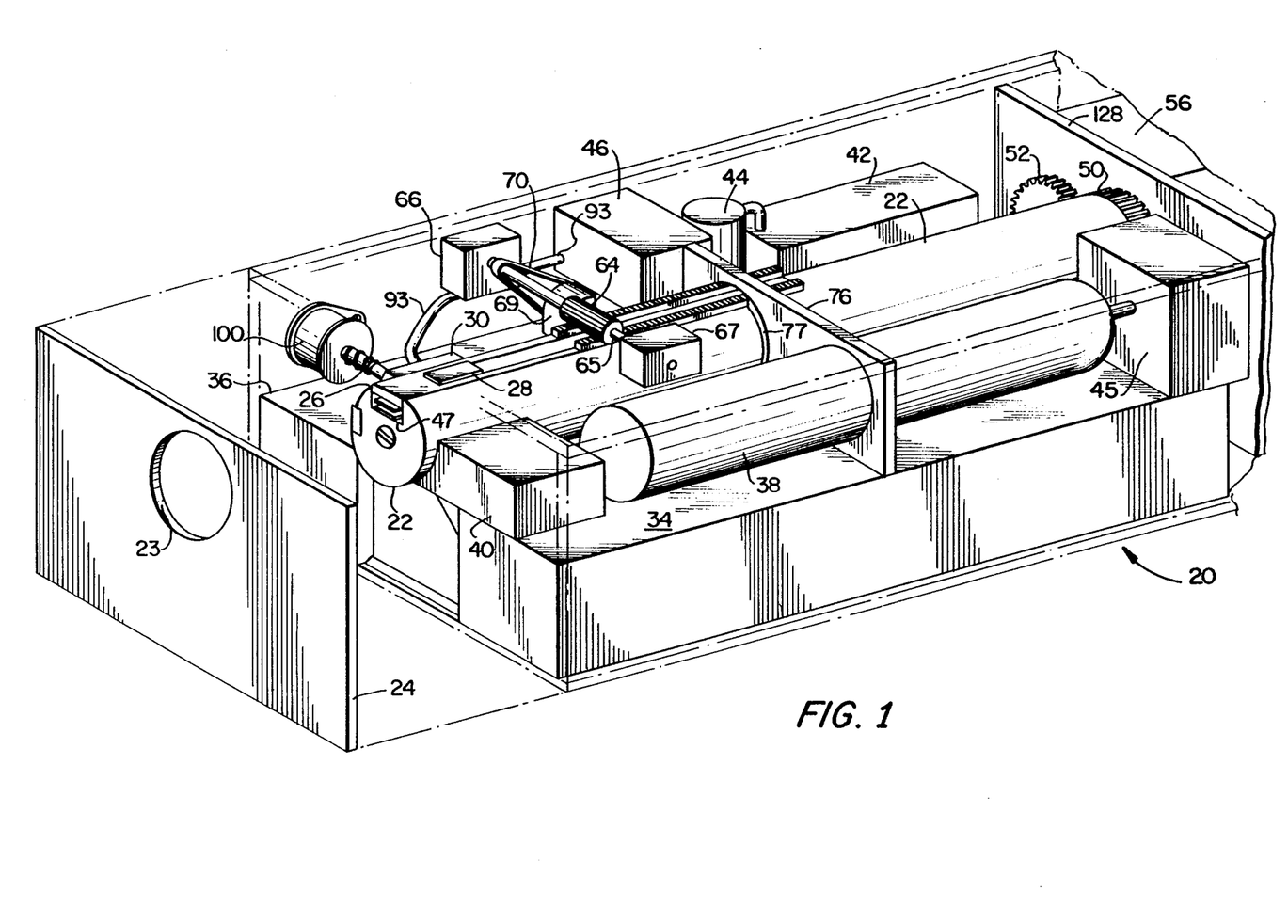
FIG. 1 is a perspective view, partly cut away, of an apparatus in accordance with the invention.
Figure 2:
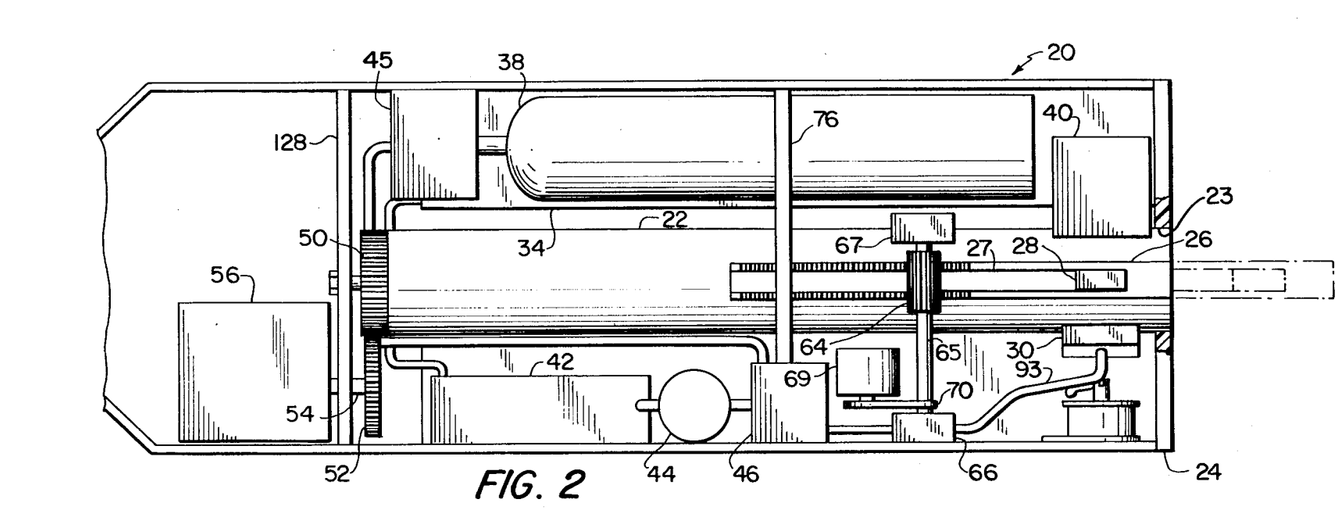
FIG. 2 is a plan view, in partial section, of the apparatus of FIG. 1.
Figure 3:
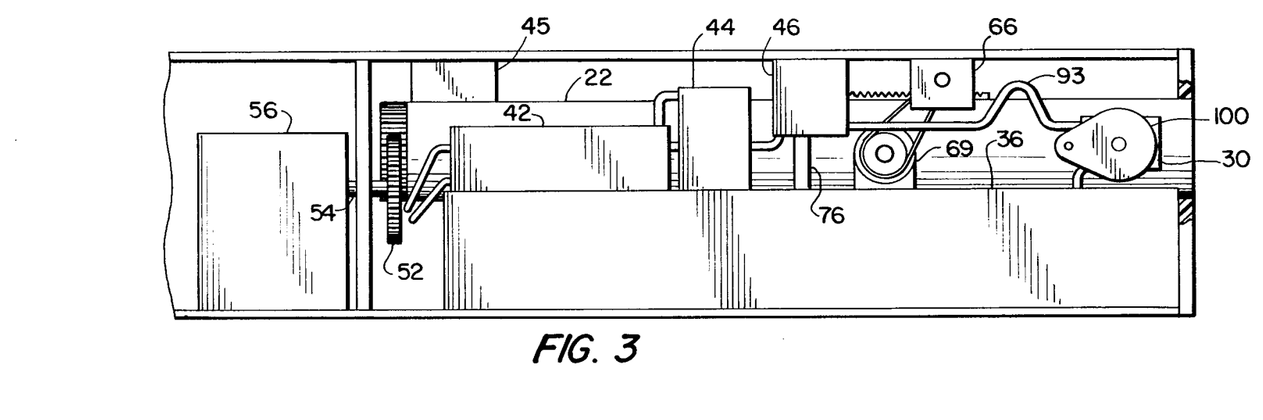
FIG. 3 is a side elevation, in partial section, of the apparatus of FIGS. 1 and 2.

As seen in FIGS. 1, 2 and 3, with holder 26 in the retracted position, pad 28 is in the position shown in FIG. 2 and the end of the holder is flush with the end of carrier 22 and the outer surface of wall 24.

Also within the housing is a wash cup 30, a de-watering device indicated generally at 32, a water storage tank 34 for containing a supply of wash water, a reservoir 36 to receive used wash water, an air tank 38 which contains pressurized air to control the washing action, and a measuring device 40 which contains a light source and photocell to accomplish the reflectance test. The housing also contains a metering pump 42 and a valve 44 for delivering a measured amount of water to a discharge chamber 46. Additionally, a pressure regulator and valve mechanism 45 controls the flow of pressurized air to discharge chamber 46 to control the washing action.

The inner end of carrier 22 is provided with a toothed ring forming a gear 50 which engages a gear 52. Gear 52 is mounted on the output shaft 54 of a drive motor 56 which can also contain reduction gearing, if desired.

Figure 4:
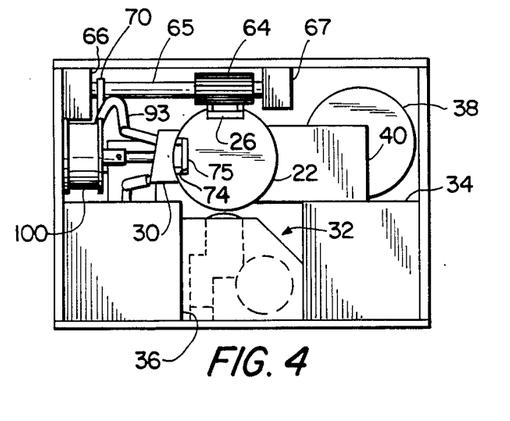
FIG. 4 is an end elevation of the apparatus of FIGS. 1-3.

As carrier 22 rotates, it is capable of carrying holder 26 with its strip 27 and pad 28 counterclockwise to four different stations which are easily recognized in FIG. 4. The first station is the receiving station at which strip 27 exists in FIG. 2 and, as viewed in FIG. 4, is at the upper position corresponding to the 12:00 position on a clock. The second station is at the 9:00 position, 90° counterclockwise removed from the first station, at which the washing of the pad 28 occurs. The third station, at the 6:00 position, is the de-watering station and the fourth position, at the 3:00 location, is the measuring station. The drive motor 56 is energized in such a way that strip 27 and pad 28 remain at each of the stations for a predetermined time as will be described.

Figure 8:
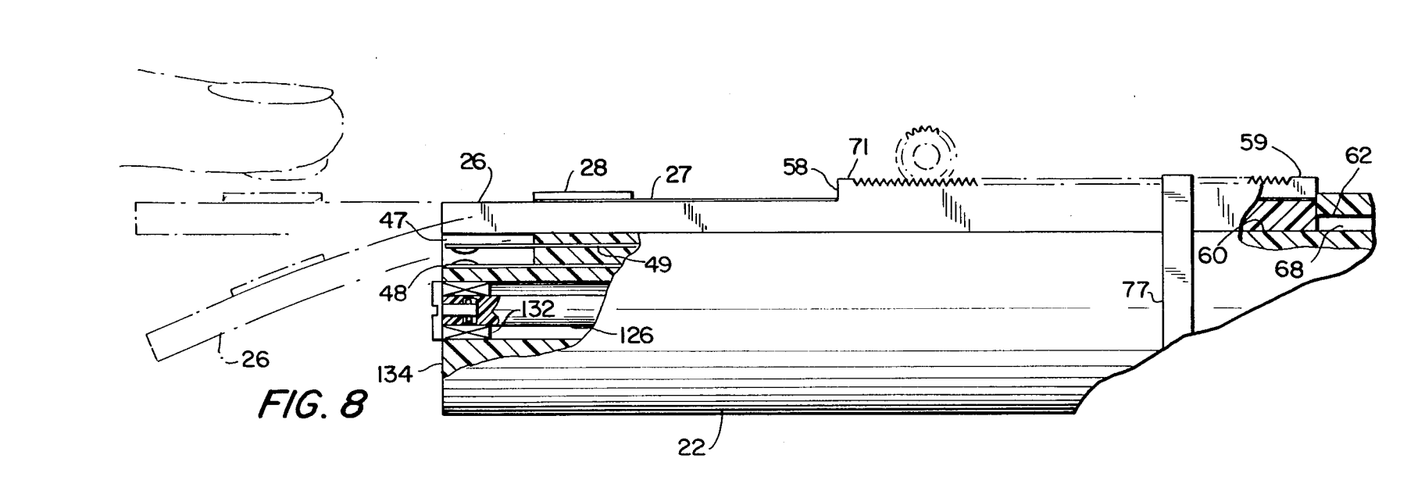
FIG. 8 is an enlarged partial side elevation of the front portion of the carrier structure of FIG. 5.
Figure 9:
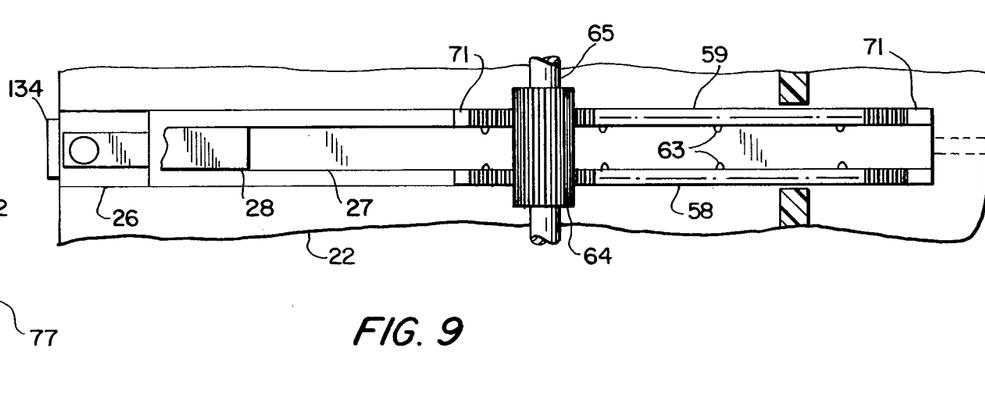
FIG. 9 is a top plan view of the structure of FIG. 8.
Figure 10:
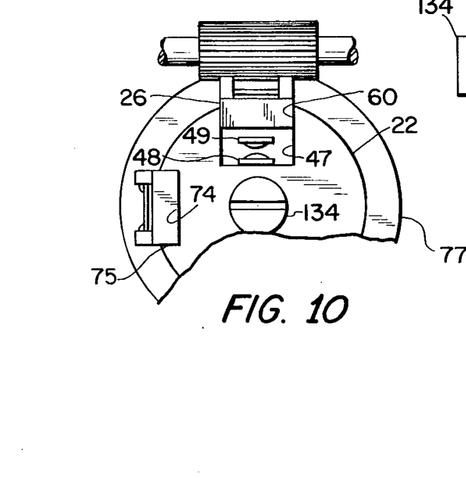
FIG. 10 is an end elevation of the structure of FIGS. 8 and 9.

The mechanism for receiving and holding strip 27 is more clearly shown in FIGS. 8, 9 and 10 when viewed in conjunction with FIGS. 2 and 3. As seen in these figures, holder 26 is an elongated body having upstanding side walls 58 and 59 extending along a portion of the length of the body, the upper edges of walls 58 and 59 being serrated along most of their lengths except for flat end portion 71. Between these side walls is a flat surface which receives strip 27 with pad 28 disposed near the outer end of the holder. As seen in FIG. 10, carrier 22 is provided with a recess 60 which slidably receives holder 26. In addition, carrier 22 has an elongated bore 68 extending axially away from recess 60 to slidably receive a guide rod 62 which is unitarily formed on and protrudes from the end of holder 26.

Also as seen in FIGS. 8 and 10, a small cavity 47 is formed in the end of carrier 22 adjacent and below holder 26. A metal strip 48 is embedded in carrier 22 and has an end portion which lies on the bottom of cavity 47. A second metal strip 49 is embedded in the polymeric body of carrier 22 and extends parallel with strip 48. The end of strip 49 lies above and spaced from strip 48. Strip 49 is formed from a springy material of a type used in electromagnetic relays, such as phosphor bronze, and both of strips 48 and 49 are provided with electrical contact members at the ends in cavity 47.

At the other end of carrier 22 a circular boss 53 of plastic protrudes through an opening in gear 50, positioning the gear and providing an insulating passage for the other ends of strips 48 and 49, reduced width portions of which protrude beyond boss 53 toward wall 128. Spring contacts 55 and 57 pass through wall 128 and are bent in an L-shape in the direction of counterclockwise movement of the carrier, the bent portions being positioned so that they are contacted by the ends of strips 49 and 48 when the carrier is in the receiving position as shown. Wires 61 connect the spring contacts to a control circuit.

Holder 26 is made of a polymeric material which is reasonably flexible so that when it is in its extended position illustrated in phantom lines in FIG. 8 and when the distal end thereof is pressed downwardly by pressure of a finger against pad 28, the holder bends into a shallow curve. The lower surface of holder 26 thus enters cavity 47 and presses downwardly on strip 49, bending that strip until it makes contact with strip 48. If the carrier is in the receiving position such that the other ends of strips 49 and 48 are in contact with spring contacts 55 and 57, a circuit is completed between wires 61. These wires are connected to the control circuit to provide a start signal upon completion of this circuit, thus initiating the timing sequence as soon as a finger with a sample of blood thereon is pressed onto pad 28.

An elongated spur gear 64 is mounted on a shaft 65 which is supported in journal blocks 66 and 67 on the housing. Shaft 65 is rotatably driven, in either direction, by a small electric motor 69 mounted on tank 36 and coupled to the shaft by an elastic drive belt 70. The teeth of gear 64 engage the serrations along the upper edges of walls 58 and 59 so that when motor 69 is energized in the appropriate direction, the holder 26 is caused to move axially, presenting a portion of the length of the holder beyond end wall 24. The extent of this movement is sufficient, as determined by the length of the serrated portions of walls 58 and 59, to extend the holder so that pad 28 protrudes well beyond end wall 24. The movement is limited by non-serrated portions 71 and movement in the opposite direction is also limited by the abutment of the inner end of holder 26 against the end of recess 60. In either direction, if motor 69 remains energized when one of these limits is reached, band 70 simply acts as a slip clutch. When the holder is in its extended position, the strip and pad can be inserted in the holder so that the end with pad 28 is close to the outer end of the holder and most of the remainder of the strip lies between walls 58 and 59. The inner surfaces of walls 58 and 59 are provided with a plurality of inwardly protruding bumps 63 beneath which the strip is slipped to hold it in place. The holder and carrier 22 are preferably formed from polymeric materials such as nylon or Teflon which have relatively low coefficients of friction.

As seen in FIGS. 4 and 10, a second recess 74 is formed in carrier 22 to receive a second holder 75 similar to holder 26 but lacking serrated side walls such as 58 and 59. The second recess is disposed 90° away from recess 60 in the counterclockwise direction, as viewed in FIG. 4, to receive a manually inserted holder carrying a strip which has no blood sample applied to its reagent pad. This "advance" strip can then act as a standard to be sure that the instrument is properly calibrated.

Figure 11:
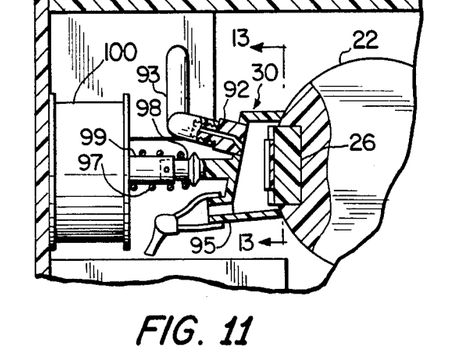
FIG. 11 is a partial end elevation, partly in section, of a washing cup structure usable in the apparatus of FIGS. 1-4.
Figure 12:
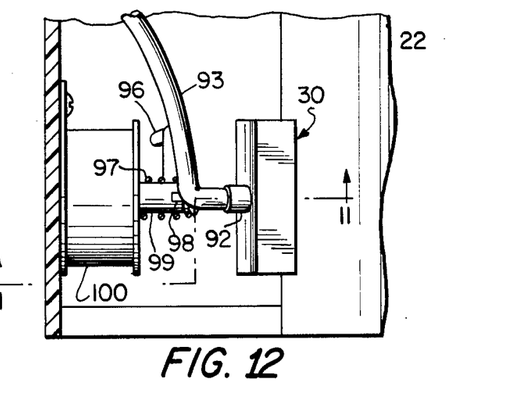
FIG. 12 is a top plan view of the portion of the apparatus including the washing structure of FIG. 11.
Figure 13:
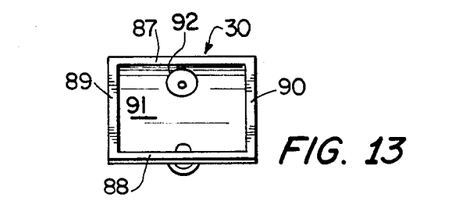
FIG. 13 is a partial side elevation along line 13—13 of the washing cup structure of FIG. 11.

The arrangement of the washing apparatus is illustrated in more detail in FIGS. 11, 12 and 13. In those figures, carrier 22 is illustrated with holder 26 rotated 90° to the wash position. The wash mechanism includes a wash cup 30 which is a generally rectangular body having an open side with inclined upper and lower edges 87, 88 to conform to the slope of carrier 22 and arcuate side edges 89 and 90 which are curved to also conform to the curvature of carrier 22 on axially opposite sides of pad 28. A back wall 91 of the wash cup is provided with an inlet nozzle 92 having a central opening through which water can be conducted for the purpose of spraying the surface of pad 28. Nozzle 92 is connected to a hose 93 which leads to the outlet of discharge chamber 46. Before washing, a measured amount of water, e.g., about 4 cc., is delivered by a positive displacement pump 42 through valve 44 to chamber 46. When washing is to be accomplished, valve 48 operates to apply air under pressure to tank 46, forcing the water from chamber 46 through tube 93 to wash cup 30 wherein the water is forcibly sprayed in a stream against the pad. At the lower end of back wall 91 is a drain opening 95 which is connected by a hose 96 to tank 36. After the wash water has been expended, continued flow of air under pressure forcibly drains the wash cup.

Cup 30 is supported on an arm 98 which is connected to the movable plunger 99 of a solenoid 100. When energized, solenoid 100 retracts plunger 99 and, with it, arm 98 and wash cup 30 so that rotation of carrier 22 can proceed without any interference between the forward edges of cup 30 and protruding portions of holder 26. When the solenoid is de-energized, a compression coil spring 97 surrounding plunger 99 and acting against an enlargement on arm 98 presses the cup against carrier 22.

It will be observed that tubing 93 is provided with an upwardly extending U-shaped bend to permit movement of cup 30 and also to prevent gravity feed of water from chamber 46 into the wash cup.

Figures 14, 15:
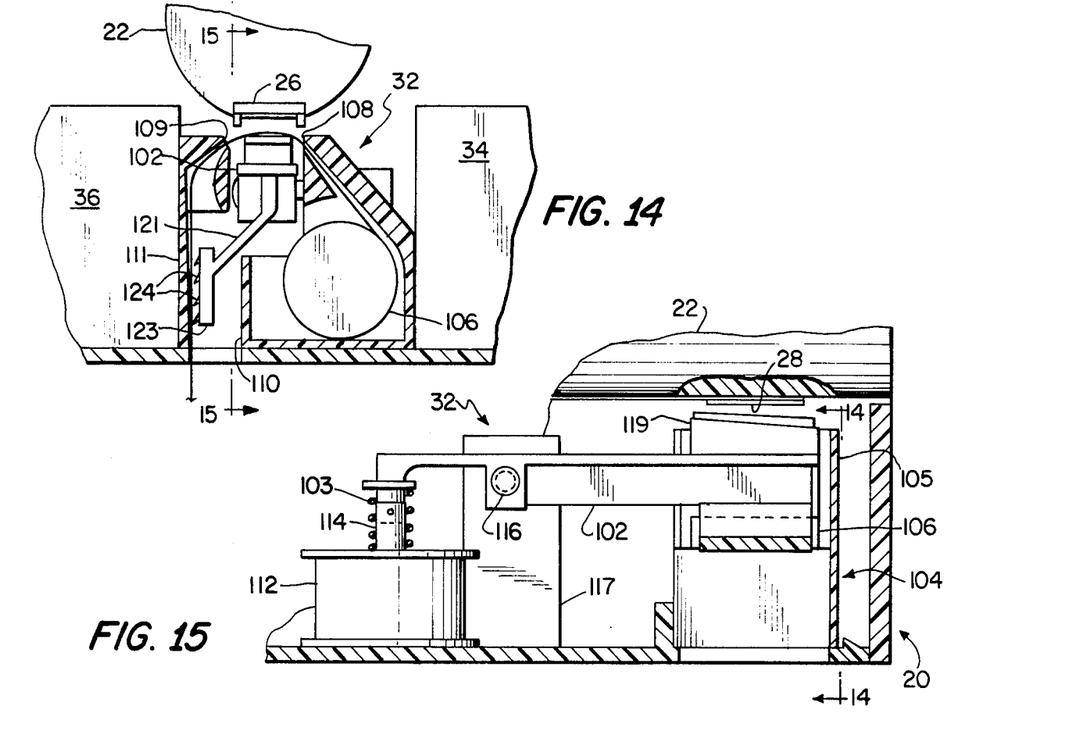
FIG. 14 is an enlarged end elevation, partly in section along line 14—14 of FIG. 15, of a de-watering apparatus usable in the apparatus of FIGS. 1-4.
FIG. 15 is a side elevation of the de-watering apparatus of FIG. 14.

A de-watering mechanism is shown in FIGS. 14 and 15, the de-watering technique used in this embodiment of the apparatus being a blotting operation. The blotting mechanism indicated generally at 32 includes two major portions, a solenoid-activated blotting arm 102 which is permanently mounted within the housing of the testing apparatus 20 and a blotting paper cartridge 104 which can be removed from the apparatus and can be either refillable or replaceable. The paper cartridge 104 includes a housing 105 of polymeric material which contains a reel of blotting paper 106. Housing 105 is provided with a chamber to receive the reel of blotting paper, the upper end of the storage chamber being formed into a guide slot 108 through which the paper extends, bridging a gap between slot 108 and a similar inlet slot 109. The blotting paper then continues down the inside of the housing and emerges through a discharge slot 110 at the bottom of housing 105 which is aligned with a slot in the bottom of the housing of apparatus 20. It will be observed that a wall 111 along the discharge side of housing 105 has an inner surface which increases in thickness toward the discharge opening, thereby forming an inwardly and downwardly sloping wall.

The blotting mechanism fixedly mounted within the housing includes a solenoid 112 having a plunger 114 which is pivotally connected to one end of arm 102 and which is surrounded by a compression coil spring 103. Arm 102 is pivotally mounted on a pivot pin 116 which is supported in a mounting block 117 supported on the housing. The other, longer arm of blotting lever 102 is generally T-shaped in cross section, the transverse portion of the T supporting a blotting pad 119 which has an inclined upper surface. Thus, when solenoid 112 is actuated to retract plunger 114, arm 102 pivots in a counterclockwise direction, as viewed in FIG. 15, moving the inclined surface toward pad 28 positioned above it. The inclined upper surface of the blotting pad is thus substantially parallel with the surface of pad 28 when contact is made. The paper 106 from cartridge housing 105 extends across the upper surface of pad 119 and is brought into intimate contact with pad 28 to perform the blotting operation. Pad 119 is preferably made of a relatively soft, foam polymeric material to enhance the blotting operation.

Arm 102 also carries a feed mechanism to advance the blotting paper. This mechanism includes a diagonally extending arm 121 carried by the vertical portion of arm 102, arm 121 ending in a generally vertically extending plate 123 which is provided with a series of protruding points 124 extending toward that portion of the blotting paper leading to the discharge opening. When arm 102 moves upwardly, plate 123 with points 124 also move upwardly, the points being downwardly inclined so that they simply slide along the inner surface of the blotting paper, creating substantially no motion of the paper. Also, points 124 are moving away from the inner surface of wall 111 because of the decrease in thickness thereof in the upward direction. After the blotting is accomplished and solenoid 112 is de-energized, spring 103 causes arm 102 to swing downwardly, permitting points 124 to engage the blotting paper and cause it to move downwardly, extracting a fresh supply from reel 106 with each such motion. Thus, stepwise increments of new blotting paper are presented to the space between pad 119 and reagent pad 28. After a test has been accomplished and holder 26 has been moved away from the de-watering station, solenoid 112 can be energized three or four times to activate the feeding mechanism repetitively, thereby moving a totally new blotting paper supply into position for the next test.

The measuring device 40 at the fourth station need not be described in detail since it is a conventional device which involves illuminating the pad 28, receiving light reflected from the pad and producing an electrical signal representative of the pad color. That signal is coupled by wires, not shown, to an analysis device in the rear portion of the apparatus housing.

A mounting arrangement for carrier 22 is illustrated in FIGS. 5, 6, 7 and 8. An elongated rod 126 is mounted in a transverse wall 128 extending across the interior of the housing. Rod 126 is threaded at one end and held in position by nuts 129. Gear 50, which is attached to the inner end of carrier 22, has a roller bearing 130 centrally mounted therein, the bearing being slidably supported on rod 126. At the other end, carrier 22 has a second roller bearing assembly 132 similarly supported at the distal end of rod 126. An opening through the outer end of body 22 receives a quarter-turn fastener 134 which engages an internally slotted opening in the distal end of rod 126 to keep body 22 on the rod. The fastener is preferably latched with a left-handed movement to prevent removal with normal counterclockwise motion of body 22.

An intermediate wall 76 extends across the interior of the housing of apparatus 20 and has an opening through which air tank 38 extends. Wall 76 also has an opening which receives a ring 77 attached to and surrounding carrier 22, ring 77 having a diameter which is at least as large as the diameter of a circle concentric with carrier 22 and passing around the outer limits of walls 58 and 59. Ring 77 can be made of metal or low friction plastic so as to freely slide in opening 76 as carrier 22 rotates, providing support at the approximate midpoint of carrier 22.

Figure 5:
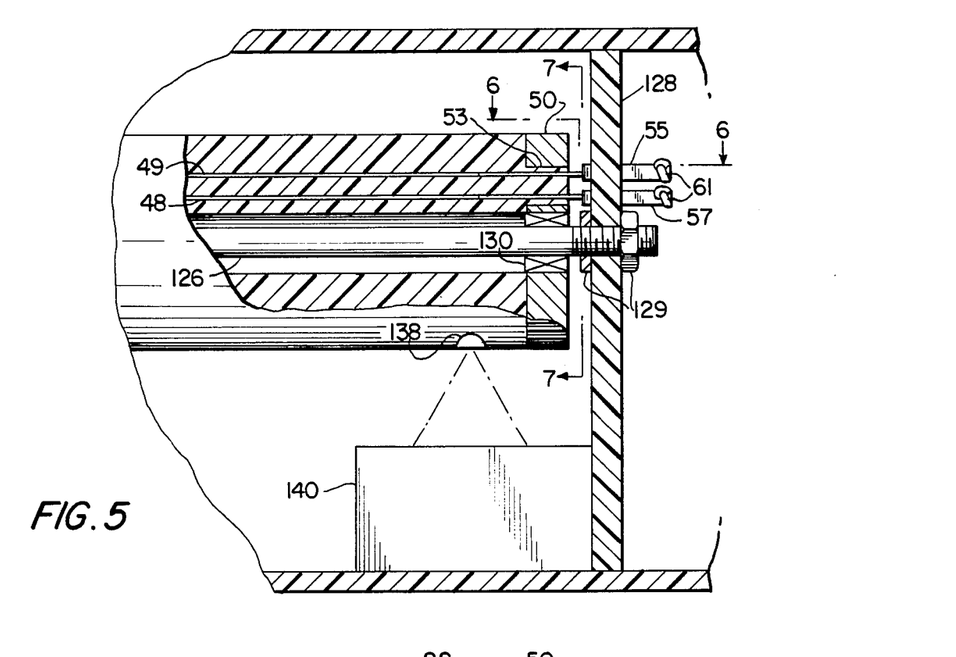
FIG. 5 is an enlarged partial side elevation, partially in section, shownning the mounting arrangement for a rotatable carrier usuable in the apparatus of FIGS. 1-4.
Figure 6:
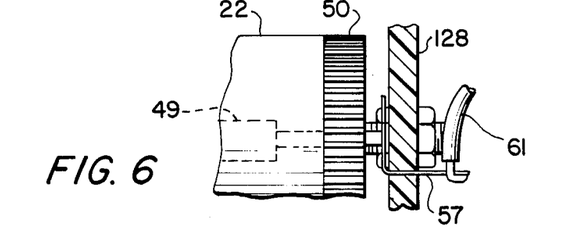
FIG. 6 is a fragmentary top plan view of a portion of the carrier of FIG. 5 taken along line 6—6.
Figure 7:
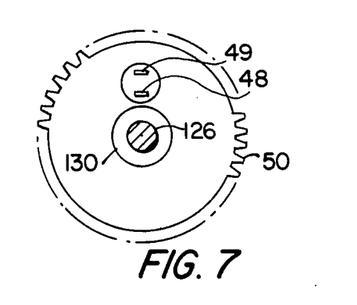
FIG. 7 is an end elevation, partly in section, along line 7—7 of FIG. 5.

FIG. 5 also illustrates a mechanism for proper rotational positioning of body 22 including four orthogonally disposed reflective regions 138 and an optical sensor 140. Sensor 140 includes a light source and a photocell positioned to project light toward and receive light from, respectively, reflective regions 138. The regions can be simple dots, lines or bar codes, but in any event, reflect light from the source to the photocell within sensor 140 to provide a signal representative of the proper positioning of the body 22 about its rotational axis.

Before discussing the control aspects of this apparatus, the overall operation will be briefly reviewed. A test is initiated by inserting a test strip with a reagent pad into holder 26 when the holder is in its extended position. The test strip must be positioned initially so that pad 28 is outside of the housing and rests on the protruding portion of holder 26. A second strip is inserted into holder 75 with its pad similarly positioned. A sample of blood to perform the test is obtained by puncturing a portion of the body such as the fingertip, using a device such as a MONOLET or AUTOLET puncturing device sold for this purpose. The blood sample is then placed on pad 28 by pressing the punctured portion of the finger downwardly against the pad, causing holder 26 to bend into cavity 47 so that the contacts on strips 48 and 49 are closed. This produces a signal which causes motor 69 to be energized and starts the timing of the reaction. Thus, the strip is immediately slid into the holder until the end of the strip abuts the inner end of recess 60. The timing mechanism retains the holder in this location for an interval of 60 seconds to permit the blood to react with the reagent substances provided on the pad. Near the end of this interval, the "standard" pad is washed and chamber 46 is refilled with water. At the conclusion of the 60-second interval, carrier 22 is rotated 90° so that the pad 28 is presented to the wash station and the wash process is commenced by projecting a stream or spray of water through nozzle 92 and onto the pad, the wash being accomplished for a predetermined interval, for example, one second and using a measured volume of water supplied by pump 42 which can be, for example, 4 cc. Sufficient air pressure from tank 38 is supplied to inject the water and to then flush excessive used wash water through the drain opening and into tank 36. While pad 28 is being washed, the pad on the "standard" strip is blotted by energization of solenoid 112.

Wash cup 30 is then retracted by energizing solenoid 100 and carrier 22 is rotated to the de-watering station at which solenoid 112 is energized to pivot arm 122 so that pad 119 moves upwardly, pressing blotting paper 106 against pad 28 and removing excess water therefrom. Energization can be repeated, advancing the blotting paper and reblotting the pad for a predetermined number of times. It is, however, not necessary to dry the pad; it is simply necessary to remove excess water which would effect the reflectivity of the pad. While pad 28 is at the blotting station, the standard pad is at the measuring station where its reflectivity is measured.

Carrier 22 is then rotated again to convey pad 28 to the measuring station at which a beam of light is employed to illuminate the pad and a photocell is used to receive the light from the pad, producing an electrical signal which has a magnitude proportional to the color of the pad within the range of interest. The reflectometer portion of the apparatus is conventional and will not be described in detail. However, the signal is employed to produce a display of the glucose level as revealed by the color change undergone by the reagent pad. Preferably, the electronics used for processing the reflectometer signal includes one or more memory locations for storing one or more correction factors which can be inserted to correct the signal for the individual patient. This correction factor is needed to correct the glucose level calculation to account for various conditions which can alter the correlation curve and so that the displayed value can be treated as a chemical value.

Figure 16:
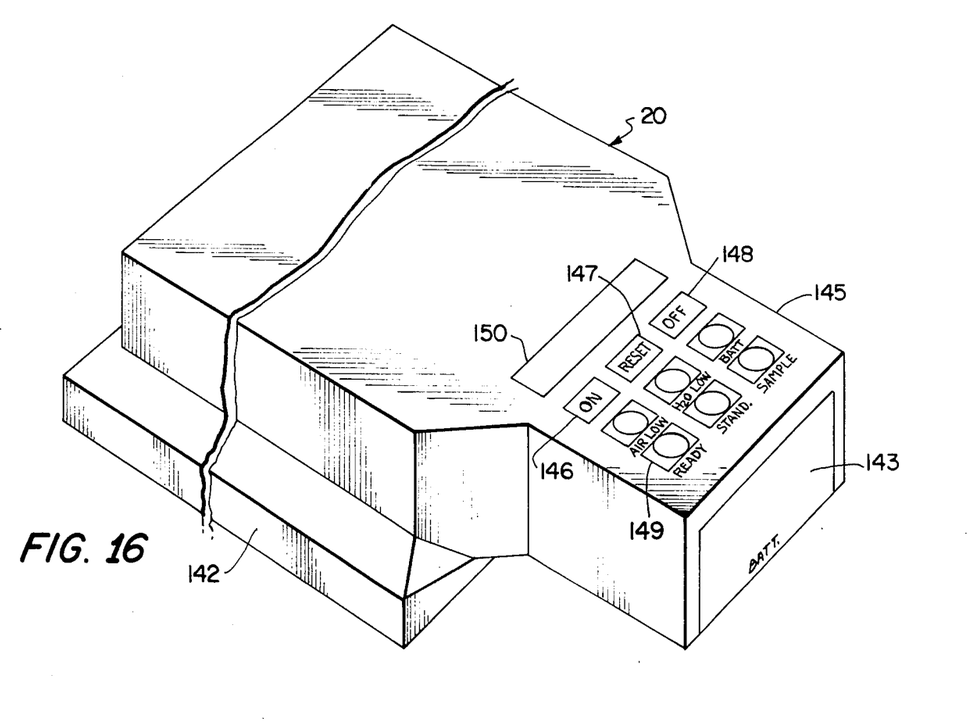
FIG. 16 is a perspective view of the exterior of an apparatus in accordance with the invention in a charging base.

FIG. 16 shows an overall perspective view of the exterior of an apparatus 20 mounted in a charging base 142 which can be used to recharge batteries housed in unit 20 behind a cover 143. Base 142 can also contain circuitry to monitor functions in unit 20.

Unit 20 has a reduced-size end portion 145 which can act as a handle and which contains the test and control electronics to perform the functions discussed above. The control apparatus is relatively simple and can either be hardwired discrete components or a combination of some hardwired components with a programmed microprocessor, the latter being preferred. The upper face of handle portion 145 includes push-buttons 146, 147 and 148 to turn the unit on, reset the internal logic and to turn the unit off. An LCD type of display is provided to indicate glucose level or other characteristics which can be measured and displayed.

A series of lights are provided as illustrated to indicate conditions of the apparatus including adverse conditions such as inadequate air pressure in tank 38, insufficient water in tank 34 or inadequate power in the batteries to perform a test. A "ready" light 149 which is also a push-button switch illuminates to indicate that the device is in condition to perform a test. Lights labeled "STAND." and "SAMPLE" are used to indicate that the reading being displayed on display 150 at the time when one of those lights is illuminated is a reading of the standard, which should indicate zero glucose level, or of the blood sample.

Figure 17:
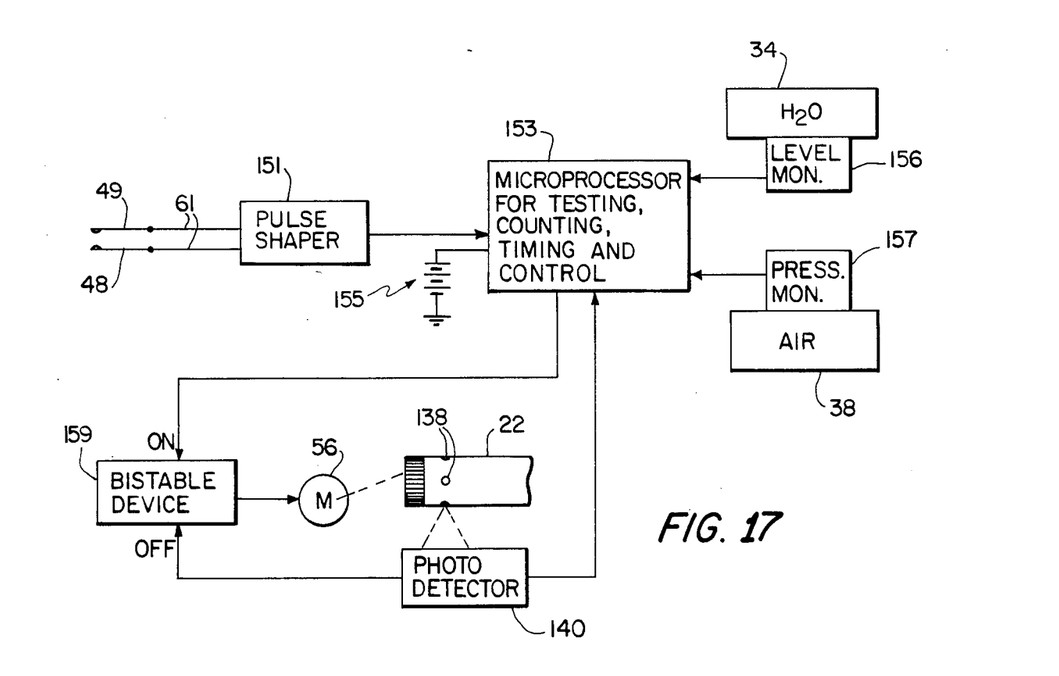
FIG. 17 is a schematic diagram, partly in block form, of a control apparatus usable in conjunction with the present invention.

FIG. 17 shows an overall schematic diagram of the control apparatus including strips 48 and 49 which, when brought together by bending holder 26, produce a signal on wires 61 which is delivered to a pulse shaper 151 which produces a pulse for delivery to microprocessor 153. The batteries indicated generally at 155 are connected to provide voltage to microprocessor 153, to strips 48 and 49 and also to the other components by wires which are not illustrated in FIG. 17.

Water and air tanks 34 and 38 are provided with level and pressure monitors, respectively, 156 and 157 which supply inputs to microprocessor 153. An output of microprocessor 153 is supplied to a bistable device 159, which can be a relay, to energize drive motor 56 to cause rotation of carrier 22. The photoresponsive device 140, as previously described, senses the presence of reflective regions 138 on carrier 22 and provides signals to de-energized bistable device 159 and to provide an "off" signal to microprocessor 153.

Figure 18:
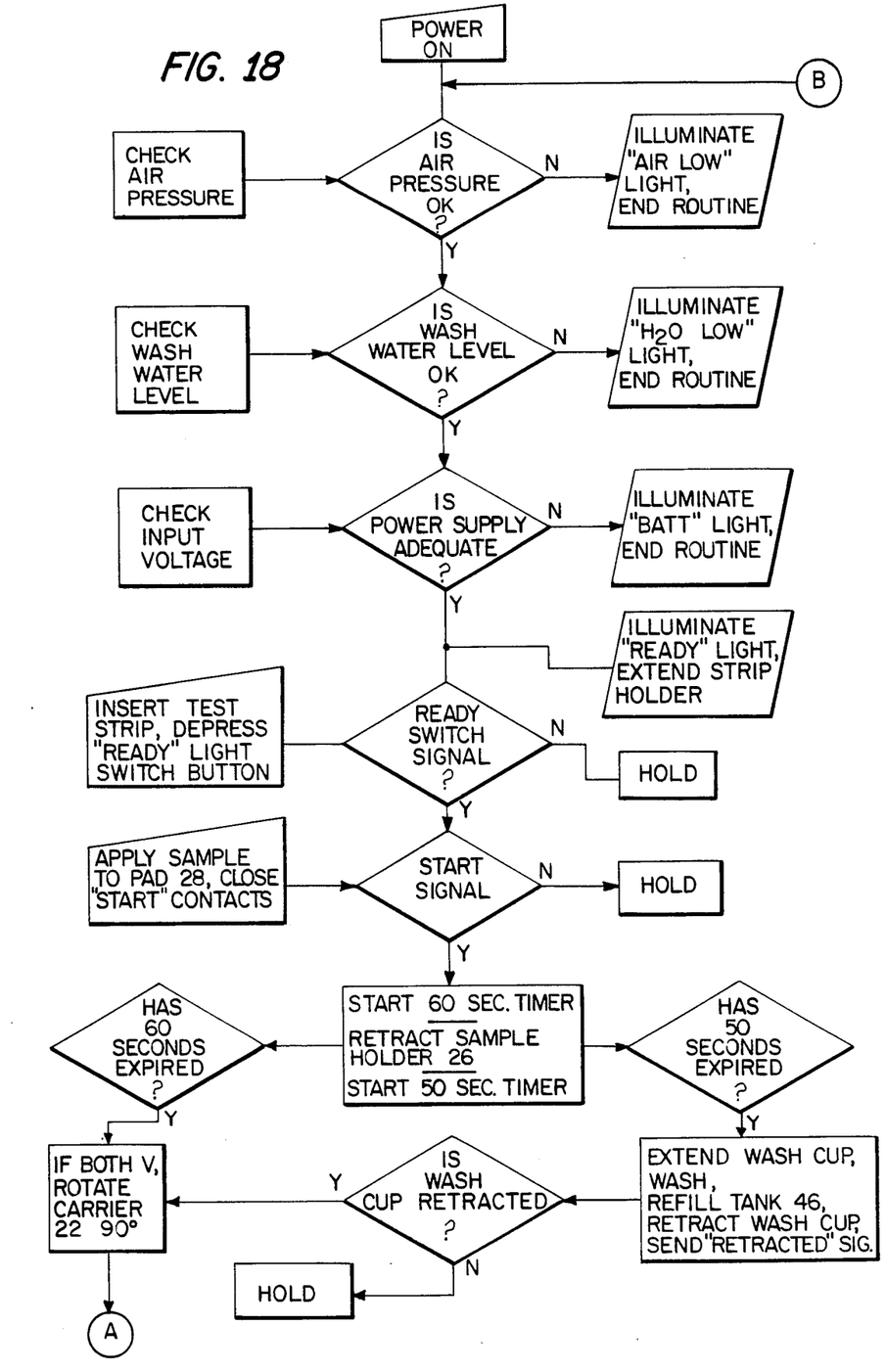
FIGS. 18 and 19, taken together, show a functional block diagram of the sequence of steps usable in a control system for the apparatus of the invention.
Figure 19:
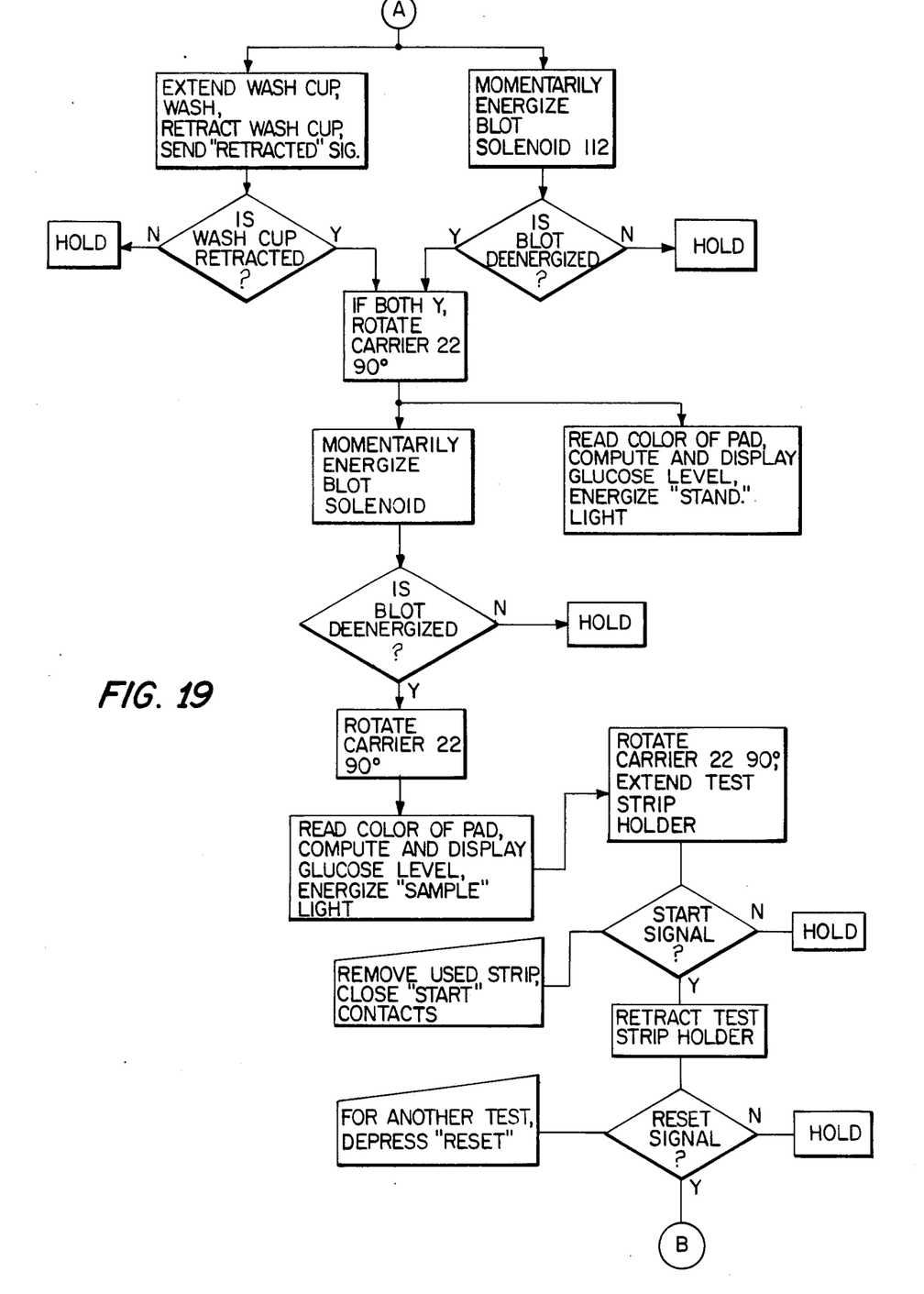

The functional aspects of the system and the general outline for programming a microprocessor for performing the necessary functions is shown in FIGS. 18 and 19. Initially, as soon as the power is turned on by depressing switch 146, the air pressure, water level and input voltage are checked and, if these supplies are adequate, the "ready" light is illuminated and the motor 69 is energized to extend strip holder 26 to receive a strip. If any of these is inadequate, a light indicating which is inadequate is illuminated and the routine is ended, preventing the possibility of performing a test with inadequate air, water or power. When the ready light is illuminated and holder 26 is extended, a fresh test strip is inserted into the holder with the pad toward the distal end of the holder, as shown. The user then depresses the ready light switch button which permits the microprocessor to supply voltage to strips 48 and 48. A sample of blood can then be applied to pad 28, depressing sample holder 26 and closing the contacts on strips 48, 49 to produce a start signal. If no start signal is provided, the routine is in a hold status. As soon as the start signal is supplied, the 60 second timer is started, the sample holder 26 is retracted and a shorter timer having an interval of about 50 seconds is started. At the end of the 50 second interval, the wash cup is extended toward carrier 22, the standard pad is washed, tank 46 is refilled, the wash cup is retracted, and a "retracted" state is flagged. At the expiration of the 60 second interval, assuming that a wash cup retracted flag has been set, the carrier is rotated through 90 degrees.

Continuing onto FIG. 19, after rotation of carrier 22, the wash cup is extended, pad 28 is washed, the wash cup is retracted and the "retracted" flag is set. Meanwhile, blot solenoid 112 is energized to blot the standard pad. After retraction of the wash cup and de-energization of the blot solenoid, carrier 22 is rotated an additional 90 degrees. The blot solenoid is again energized and the photoresponsive unit 40 is activated to read the color of the standard pad, compute and display the glucose level and energize the "stand." light. After de-energization of the blot solenoid, the carrier is rotated an additional 90 degrees and the color of pad 28 is read, the glucose level is displayed and the "sample" light is energized. At the conclusion of this measurement, the glucose reading can be retained on display 150 and the carrier is rotated a further 90 degrees to its original position and the sample holder is extended for removal of the test strip and insertion of a further strip for a subsequent test. Removal of the strip depresses the holder, again closing the contacts on strips 48, 49 to provide another start signal. However, this start signal is interpreted as an "end" signal in response to which the strip holder is retracted to prevent accidental damage to it. If no further test is to be run, the new strip should, of course, not be inserted. Instead, the unit is simply de-energized by depressing "OFF" switch 148. If a new test is to be run, the new strip is inserted and "Reset" switch button 147 is depressed causing the routine to return to the beginning to check for adequate air, water, and power. The standard strip should also be removed and replaced.

While one advantageous embodiment has been chosen to illustrate the invention, it will be understood by those skilled in the art that various changes and modifications can be made therein without departing from the scope of the invention as defined in the appended claims.

What is claimed is:

1. An apparatus for performing a test to determine the glucose level in a sample of blood placed on a reagent pad attached to an elongated test strip of flexible material, the apparatus comprising the combination of individual means respectively defining a receiving station, a wash station, a de-watering station, and a measuring station in spaced relationship from each other;

carrier means for holding a test strip having a reagent pad thereon, said carrier means being movable to transport a test strip having a reagent pad thereon to each of said stations in sequence, said carrier means comprising       a generally cylindrical body having a central axis, said stations being disposed around the circumference of said body;

means for mounting said body for rotation about said central axis;

an axially extending holder on said body for receiving and retaining said pad, said holder including means for receiving and retaining a test strip having a reagent pad thereon comprising an elongated body having a flat portion dimensioned to receive (said) a test strip having a reagent pad thereon, said elongated body being slidably mounted on said cylindrical body for axial movement between a retracted position and an extended position; and means for controllably moving said elongated body between said retracted and extended positions, said means defining a receiving station located at the same axial position with respect to said central axis as the extended position of said elongated body and said individual means defining a wash station, a de-watering station and a measuring station being located at the same axial position with respect to said central axis as the retracted position of said elongated body, control and drive means for moving said carrier means to transport a reagent pad mounted on a test strip elongated body to said stations and to hold (said) such a test strip sequentially at each of said individual means defining a watering station, a de-watering station and a measuring station while in said retracted position and at said means defining a receiving station while in said extended position for preselected intervals of time, said means defining a wash station including means for washing a reagent pad mounted on a test strip retained by said elongated body when said carrier is moved to present said elongated body to said (said) means defining a wash station, said means defining a de-watering station including means for removing superficial water remaining after washing from a reagent pad mounted on a test strip retained by said elongated body when said (pad) elongated body is moved to said means defining a de-watering station, said means defining a measuring station including means for producing a signal representative of color characteristics of a reagent pad mounted on a test strip retained by said elongated body when said elongated body is moved to said means defining a measuring station, and means for receiving said signal and for producing a display representative of color characteristics of a reagent pad mounted on a test strip which is carried by said elongated body.

2. An apparatus according to claim 1 wherein said means defining receiving, washing, de-watering and measuring stations are circularly spaced around said cylindrical body;

and wherein said control and drive means includes means for rotating said carrier in increments so that a test strip having a reagent pad thereon which is retained by said elongated body is moved sequentially between each of said stations.

3. An apparatus according to claim 1 wherein said means for washing includes a cup-shaped body having an open side facing toward said carrier means and being movable against said carrier;

a water supply;
a supply of air under pressure;
a discharge chamber in fluid communication with said cup-shaped body and said water supply;
means for delivering a measured quantity of water from said water supply to said discharge chamber;
valve means for introducing air under pressure from said supply of air under pressure into said discharge chamber to force water from said discharge chamber into said cup and against a reagent pad mounted on a test strip carried by said elongated body to wash a reagent pad which is so carried by said elongated body; and
drain means for draining water from said cup-shaped body.

4. An apparatus according to claim 1 wherein said means for removing superficial water includes
a strip of water-absorbent blotting paper; and
means for pressing said blotting paper against a pad mounted on a test strip which is retained on said elongated body.

5. An apparatus according to claim 1 wherein said holder comprises
wall means on said cylindrical body extending radially outwardly relative to said central axis, the upper edges of said wall means having teeth thereon;

and said apparatus further comprises
gear means mounted above said holder at said receiving station for engaging said teeth; and
said means for controllably moving said elongated body comprises means for driving said gear means to move said elongated body of said holder between said extended and retracted positions.

6. An apparatus according to claim 5 wherein said means defining receiving, washing, de-watering and measuring stations are circularly spaced around said cylindrical body;

and wherein said control and drive means includes means for rotating said carrier in increments so that a test strip having a reagent pad thereon which is retained by said elongated body is moved sequentially between each of said stations.

7. An apparatus according to claim 6 wherein said means for washing includes a cup-shaped body having an open side facing toward said carrier means and means for moving said cup-shaped body against said carrier to enclose a reagent pad mounted on a test strip which is carried by said elongated body when said elongated body is located at said means defining a wash station;

a water supply;
a supply of air under pressure;
a discharge chamber in fluid communication with said cup-shaped body and said water supply;
means for delivering a measured quantity of water from said water supply to said discharge chamber;
valve means for introducing air under pressure from said supply of air under pressure into said discharge chamber to force water from said discharge chamber into said cup and against a reagent pad mounted on a test strip carried by said elongated body to wash a reagent pad which is so carried by said elongated body; and
drain means for draining water from said cup-shaped body.

8. An apparatus according to claim 7 wherein said means for removing superficial water includes
a strip of water-absorbent blotting paper, and
means for pressing said blotting paper against a pad mounted on a test strip which is retained on said elongated body.

9. An apparatus according to claim 5 wherein said means for washing includes a cup-shaped body having an open side facing toward said carrier means and means for moving said cup-shaped body against said carrier to enclose a reagent pad mounted on a test strip which is carried by said elongated body when said elongated body is located at said means defining a wash station;

a water supply;
a supply of air under pressure;

a discharge chamber in fluid communication with said cup-shaped body and said water supply;

means for delivering a measured quantity of water from said water supply to said discharge chamber;

valve means for introducing air under pressure from said supply of air under pressure into said discharge chamber to force water from said discharge chamber into said cup and against a reagent pad mounted on a test strip carried by said elongated body to wash a reagent pad which is so carried by said elongated body; and drain means for draining water from said cup-shaped body.

10. An apparatus according to claim 5 wherein said means for removing superficial water includes a strip of water-absorbent blotting paper; and means for pressing said blotting paper against a pad mounted on a test strip which is retained on said elongated body.

11. An apparatus according to claim 6 wherein said means for removing superficial water includes a strip of water-absorbent blotting paper; and means for pressing said blotting paper against a pad mounted on a test strip which is retained on said elongated body.

* * * * *